United States Patent [19]
Habermann

[11] Patent Number: 5,359,035
[45] Date of Patent: Oct. 25, 1994

[54] BIFUNCTIONAL PROTEINS INCLUDING INTERLEUKIN-2 (IL-2) AND GRANULOCTYTE MACROPHAGE COLONY STIMULATING FACTOR (GM-CSF)

[75] Inventor: Paul Habermann, Frankfurt am Main, Fed. Rep. of Germany

[73] Assignee: Hoechst Aktiengesellschaft, Frankfurt am Main, Fed. Rep. of Germany

[21] Appl. No.: 963,040

[22] Filed: Oct. 19, 1992

Related U.S. Application Data

[63] Continuation of Ser. No. 812,838, Dec. 20, 1991, abandoned, which is a continuation of Ser. No. 181,374, Apr. 14, 1988, abandoned, which is a continuation-in-part of Ser. No. 943,432, Dec. 19, 1986, abandoned.

[30] Foreign Application Priority Data

Dec. 21, 1985 [DE] Fed. Rep. of Germany ....... 3545568
Apr. 16, 1987 [DE] Fed. Rep. of Germany ....... 3712985

[51] Int. Cl.$^5$ .................... C07K 13/00; A61K 37/02
[52] U.S. Cl. .................... 530/351; 530/395; 530/825; 530/402; 530/408; 530/409; 530/399; 930/140; 930/141; 424/85.1; 424/85.2
[58] Field of Search ........ 530/351, 395, 402, 408–409, 530/399; 930/140, 141; 424/85.1, 85.2; 514/2, 8, 12

[56] References Cited

U.S. PATENT DOCUMENTS

| | | | |
|---|---|---|---|
| 4,675,383 | 6/1987 | Murphy ............................. | 530/350 |
| 4,711,845 | 12/1987 | Gelfanl et al. ...................... | 530/351 |
| 4,738,921 | 4/1988 | Belazaje et al. ..................... | 536/27 |
| 4,784,949 | 11/1988 | Gelfanl et al. ...................... | 935/10 |
| 4,935,233 | 6/1990 | Bell et al. ........................... | 424/85.5 |
| 5,071,761 | 12/1991 | Meyer et al. ....................... | 435/69.52 |
| 5,073,627 | 12/1991 | Curtis et al. ....................... | 435/69.52 |
| 5,166,322 | 11/1992 | Shaw .................................. | 530/351 |

FOREIGN PATENT DOCUMENTS

| | | |
|---|---|---|
| 0091539A1 | 10/1983 | European Pat. Off. . |
| 0109748A1 | 5/1984 | European Pat. Off. . |
| 0118617A2 | 9/1984 | European Pat. Off. . |
| 0136489A1 | 4/1985 | European Pat. Off. . |
| 0195680 | 9/1986 | European Pat. Off. . |
| 0219839A2 | 4/1987 | European Pat. Off. . |
| 0228018A2 | 8/1987 | European Pat. Off. . |
| 0041697 | 3/1985 | Japan . |
| 8502200 | 5/1985 | PCT Int'l Appl. . |

OTHER PUBLICATIONS

Schrader et al, PNAS 83, 1986, pp. 2458–2462.
Stanley et al EMBO 4, 1985, pp. 2569–2573.
Gough et al, Eur J Biochem 169, 1987, pp. 353–358.
Taniguchi et al, CA vol. 110, 1989, #52334w.
Igamashi et al, CA vol. 107, 1987, #14899g.
Senoo et al, CA vol. 104, 1986, #220129e.
Wong et al, PNAS 83, 1986, pp. 3233–3237.

Primary Examiner—Garnette D. Draper
Attorney, Agent, or Firm—Finnegan, Henderson, Farabow, Garrett & Dunner

[57] ABSTRACT

Bifunctional proteins, obtainable by genetic manipulation, composed of an interleukin-2 and a granulocyte macrophage colony stimulating factor constituent have the biological activity of both components but are distinguished by increased stability. These proteins are thus medicaments which are suitable for the treatment of malignant neoplasms.

14 Claims, 1 Drawing Sheet

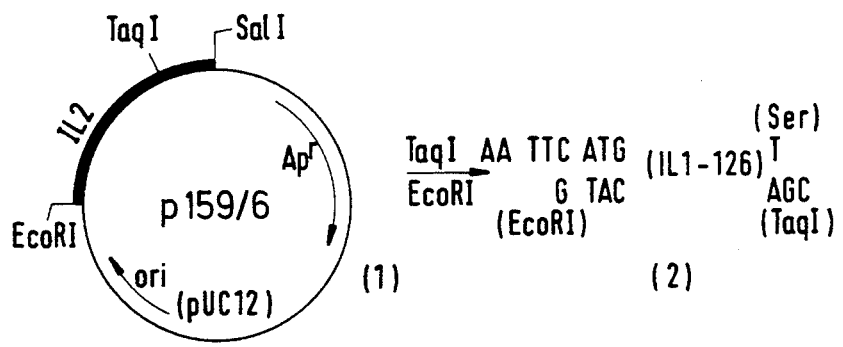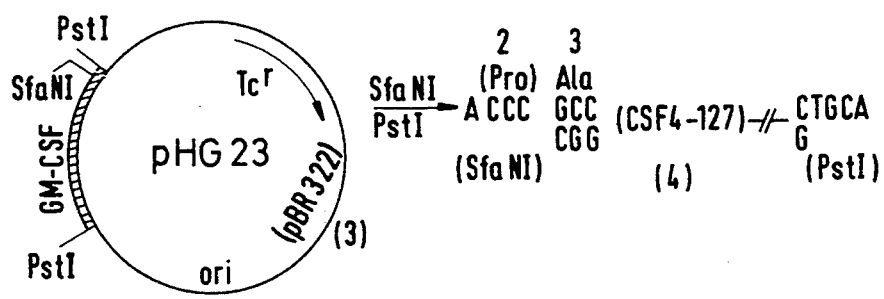
```
      128                                  (133)                          1    2
     Ile  Ile Ser Thr Leu Asp  Pro  Met Ile Thr Thr Tyr Ala Asp Asp Pro (Ala)(Pro)
   CG ATC ATC TCT ACC CTG GAC  CCG ATG ATC ACC ACC TAT GCG GAC GAT CCG  GC
      TAG TAG AGA TGG GAC CTG  GGC TAC TAG TGG TGG ATA CGC CTG CTA GGC  CGT GGG
  (TaqI)                                   (5)                          (SfaNI)
```
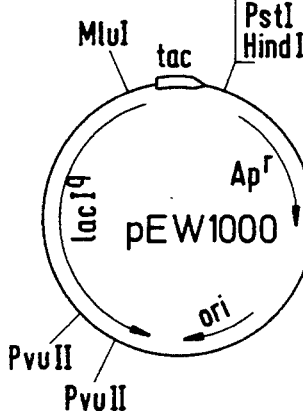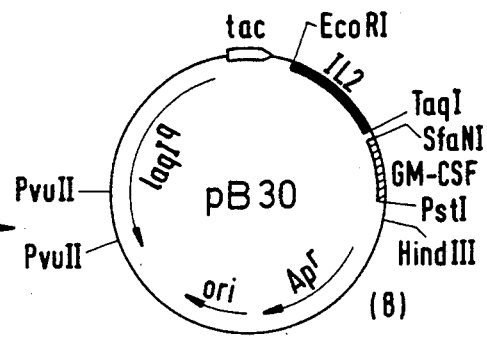

BIFUNCTIONAL PROTEINS INCLUDING INTERLEUKIN-2 (IL-2) AND GRANULOCYTE MACROPHAGE COLONY STIMULATING FACTOR (GM-CSF)

This application is a continuation of application Ser. No. 07/812,838 filed Dec. 20, 1991, now abandoned; which is a continuation of application Ser. No. 07/181,374, filed Apr. 14, 1988, now abandoned which is a continuation-in-part of application Ser. No. 943,432, filed Dec. 19, 1986, the disclosure is which is incorporated herein by reference in its entirety.

BACKGROUND OF THE INVENTION

Interleukin-2, called IL-2 hereinafter, acts as T-cell growth factor. IL-2 potentiates the activity of killer cells such as NK (natural killer) cells, cytotoxic T-cells and LAK (lymphokine-activated killer) cells.

By contrast, granulocyte macrophage colony stimulating factor, called GM-CSF hereinafter, stimulates the formation of granulocytes and macrophages from hemopoietic precursor cells. Combination of the two biological activities is of interest for human treatment with and without administration of cytostatics. However, the stabilities of IL-2 and GM-CSF differ, which may result in problems on direct administration of the two components and thus in a decrease in the therapeutic success.

The problem of the difference in stability can be solved according to the invention by linking these two proteins to a bifunctional protein.

Fusion proteins of the general formula

Met—X—Y—Z     (Ia)

or

Met—Z—Y—X     (Ib)

have already been proposed for the preparation, by genetic manipulation, of optionally modified GM-CSF in which X essentially denotes the amino acid sequence of approximately the first 100 amino acids of, preferably human, IL-2, Y denotes a direct bond if the amino acid or amino acid sequence adjacent to the desired protein allows the desired protein to be cleaved off, or otherwise denotes a bridging member which is composed of one or more genetically encodable amino acids and which allows the cleavage off, and Z is a sequence which is composed of genetically encodable amino acids and which represents the desired GM-CSF protein. It is also possible during this to make use—more or less—up to the end of the DNA sequence coding for IL-2, and thus generate biologically active IL-2—modified where appropriate —as a "by-product" (note prior-published European Patent Application with the publication number (EP-A) 0,228,018 and South African Patent 86/9557).

SUMMARY

In contrast to the earlier proposal, the invention relates not to the use of the proteins as intermediate but to the use in methods for the therapeutic treatment of the human body and to medicaments which contain fusion proteins of this type or which are composed of fusion proteins of this type. A further aspect of the invention relates to the use of these fusion proteins for the preparation of a medicament for the treatment of malignant neoplasms.

The fusion protein used according to the invention is thus composed of two biologically active components, namely of an IL-2 constituent, which can be modified in a manner known per se, on the one hand, and of a GM-CSF constituent, which can likewise be modified, on the other hand and, where appropriate, of a bridging member corresponding to the definition Y in the formulae given above. The arrangement of the two components preferably corresponds to the formula Ia. The principle according to the invention can also be used for the preparation of other novel bifunctional proteins.

BRIEF DESCRIPTION OF THE DRAWING

The FIGURE shows the construction of the plasmid pB30 which codes for a bifunctional protein according to the invention.

Modifications of the IL-2 molecule have been disclosed, reference being made here only to EP-A 0,091,539, 0,109,748, 0,118,617, 0,136,489 and 0,163,249 by way of example.

Furthermore, the not prior-published EP-A 0,219,839 proposes an IL-2 derivative in which the first seven N-terminal amino acids are deleted.

Modifications of the GM-CSF molecule have been proposed in EP-A 0,228,018.

Further alterations to the two active constituents of the molecule can be carried out in a manner known per se, mention being made here only of specific mutagenesis by way of example.

The bridging member Y advantageously has the formula II

—Asp—(aa)$_x$—Pro—     (II)

in which x denotes an integer up to about 20, and aa denotes any desired genetically encodable amino acid with the exception of cysteine.

It is advantageous in the formula II for the IL-2 constituent to be arranged at the left-hand end, and consequently the GM-CSF constituent to be arranged at the right-hand end.

Particularly preferred embodiments of Y have the amino acid sequence

—Asp—Pro—Met—Ile—Thr—Thr—Tyr—Ala—Asp—Asp—Pro or

—Asp—Pro—Met—Ile—Thr—Thr—Tyr—Leu—Glu—Glu—Leu—Thr—Ile—Asp—Asp—Pro— it again being preferable for the IL-2 constituent to be arranged at the left-hand end and the GM-CSF constituent to be arranged at the right-hand end.

The bifunctional proteins according to the invention can be expressed in a manner known per se. It is possible in bacterial expression systems for the route of direct expression to be followed. Suitable for this purpose are all known host-vector systems with hosts such as bacteria of the species Streptomyces, *B. subtills*, *Salmonella typhimurium* or *Serratia marcescens*, especially *E. coli*.

The DNA sequence which codes for the desired protein is incorporated in a known manner into a vector which ensures satisfactory expression in the chosen expression system.

It is expedient to choose for this purpose the promoter and operator from the group trp, lac, tac, $P_L$ or $P_R$ of phage λ, hsp, omp or a synthetic promoter, as described in, for example, German Offenlegungsschrift 3,430,683 and in EP-A 0,173,149. The tac promoter-operator sequence is advantageous and is now commercially available (for example pKK223-3 expression vector, Pharmacia, "Molecular Biologicals, Chemicals and Equipment for Molecular Biology", 1984, page 63).

On expression of the protein according to the invention, it may prove expedient to modify individual triplets for the first few amino acids after the ATG start codon in order to prevent any base-pairing at the level of the mRNA. Such modifications, such as deletions or additions of individual amino acids, are familiar to the expert, and the invention also relates to them.

For expression in yeasts—preferably *S. cerevisiae*—it is expedient to use a secretion system, for example heterologous expression via the α-factor system, which has been described several times.

It is advantageous for the expression of the bifunctional molecule in yeast if dibasic peptide sequences and glycosylation sites in the bifunctional protein have been destroyed by appropriate exchange of individual amino acids. This results in many possible combinations which may also influence the biological action.

The expression of IL-2 in yeast is disclosed in EP-A 0,142,268, and that of GM-CSF in EP-A 0,188,350.

The administration of the bifunctional proteins according to the invention corresponds to that of the two components. However, because of the greater stability a lower dosage is possible in many cases, the dosage being in the lower part of the range of those hitherto proposed.

The invention is illustrated in detail in the examples which follow. Unless indicated otherwise, percentage data and ratios relate to weight.

EXAMPLE 1

The plasmid p159/6 (EP-A2 0,163,249, FIG. 5; (1) the present figure) contains a synthetic gene coding for IL-2 between an EcoRI and a SalI cleavage site. The DNA sequence for this gene is represented in the said EP-A2 as "DNA sequence I". A TaqI cleavage site is located in the region of triplets 127 and 128. The IL-2 part-sequence (2) is cut out of this plasmid by cutting with EcoRI and TaqI, and is isolated.

The plasmid pHG23 (3) which codes for GM-CSF is disclosed in EP-A2 0,183,350. The GM-CSF cDNA is represented in FIG. 2 in this EP-A2. The plasmid pHG23 is obtained when the cDNA sequence is incorporated in the PstI cleavage site of pBR322, use being made of, on the one hand, the PstI cleavage site at the 5' end and, on the other hand, a PstI site introduced at the 3' end by GC tailing. The DNA sequence (4) which contains most of the GM-CSF gene is isolated from this plasmid by cutting with SfaNI and PstI.

The following oligonucleotide (5) is synthesized by the phosphite method:

|        | 128 Ile | Ile | Ser | Thr | Leu | (133) Asp | Pro | Met | Ile |     |
|--------|---------|-----|-----|-----|-----|-----------|-----|-----|-----|-----|
| CG     | ATC     | ATC | TCT | ACC | CTG | GAC       | CCG | ATG | ATC |     |
|        | TAG     | TAG | AGA | TGG | GAC | CTG       | GGC | TAC | TAG |     |
| (TaqI) |         |     |     |     |     |           |     |     |     | (5) |
|        | Thr     | Thr | Tyr | Ala | Asp | Asp       | Pro | 1 (Ala) | 2 (Pro) |
|        | ACC     | ACC | TAT | GCG | GAC | GAT       | CCG | GC      |         |
|        | TGG     | TGG | ATA | CGC | CTG | CTA       | GGC | CGT     | GGG     |
|        |         |     |     |     |     |           |     | (SfaNI) |         |

The oligonucleotide (5) extends at the 5' end the DNA sequence of IL-2, there being, however, Asp in place of Thr in position 133. At the 3' end of this oligonucleotide are located the nucleotides which have been deleted from the cDNA by cutting with SfaNI.

The preparation of the expression plasmid pEW1000 (6) is proposed in the (not prior-published) EP-A 0,227,938 (FIG. 1). This plasmid is a derivative of the plasmid ptac 11 (Amann et al., Gene 25 (1983) 167–178), in which a synthetic sequence which contains a SalI cleavage site has been incorporated in the recognition site for EcoRI. The expression plasmid pKK 177.3 is obtained in this way. Insertion of the lac repressor (Farabaugh, Nature 274 (1978) 765–769) results in the plasmid pJF118. The latter is opened at the unique restriction cleavage site for AvaI, and is shortened by about 1000 bp in a known manner by exonuclease treatment and is ligated. The plasmid pEW1000 (6) is obtained. Opening of this plasmid in the polylinker using the enzymes EcoRI and PstI results in the linearized expression plasmid (7).

This linearized plasmid DNA (7) is now ligated with the DNA fragment (2) which codes for the IL-2 sequence, with the synthetic oligonucleotide (5) and with the cDNA fragment (4). The result is the plasmid pB30 (8) which is transformed into the *E. coli* strain Mc1061. The plasmid DNA from individual clones is isolated and characterized by restriction analysis.

EXAMPLE 2

If the following synthetic oligonucleotide

|        | 128 Ile | Ile | Ser | Thr | Leu | (133) Asp | Pro | Met | Ile | Thr | Thr | Tyr |
|--------|---------|-----|-----|-----|-----|-----------|-----|-----|-----|-----|-----|-----|
| CG     | ATC     | ATC | TCT | ACC | CTG | GAC       | CCG | ATG | ATC | ACC | ACC | TAT |
|        | TAG     | TAG | AGA | TGG | GAC | CTG       | GGC | TAC | TAG | TGG | TGG | ATA |
| (TaqI) |         |     |     |     |     |           |     |     |     |     |     |     |
|        | Leu     | Glu | Glu | Leu | Thr | Ile       | Asp | Asp | Pro | 1 (Ala) | 2 (Pro) |  |
|        | CTA     | GAA | GAG | CTC | ACG | ATC       | GAC | GAT | CCG | GC      |         |  |
|        | GAT     | CTT | CTC | GAG | TGC | TAG       | CTG | CTA | GGC | CGT     | GGG     |  |
|        |         |     |     |     |     |           |     |     |     | (SfaNI) |         |  | is used in place of oligonucleotide (5) in the example 1, the result is the plasmid pB31.

EXAMPLE 3

Competent cells of the *E. coli* strain W3110 are transformed with the plasmid pB30 or pB31. An overnight culture of the strain is diluted in the ratio of about 100 with LB medium (J. H. Miller, Experiments in Molec. Gen., Cold Spring Harbor Lab., 1972), which contains 50 μg/ml ampicillin, and the grow this followed by measurement of the OD. At OD=0.5 t he culture is adjusted to a concentration of 2 mM in isopropyl-β-D-thiogalactopyranoside (IPTG) and, after 150–180 minutes, the bacteria are spun down. These bacteria are treated in a buffer mixture (7M urea, 0.1 % SDS, 0. 1M sodium phosphate, pH 7.0) for about 5 minutes, and samples are applied to an SDS polyacrylamidege gel electrophoresis plate. This confirms the expression of the bifunctional protein.

The stated conditions apply to shake cultures; for larger fermentations it is expedient to modify the OD values and nutrient media and vary the IPTG concentrations appropriately.

EXAMPLE 4

*E. coli* W3110 cells which contain the plasmid pB30 or pB31 are, after induction, spun down, resuspended in sodium phosphate buffer (pH 7) and again spun down. The bacteria are taken up in the same buffer and then disrupted (French Press, ®Dynomill). The disrupted cells are spun down. The supernatant and sediment are analyzed by SDS polyacrylamide gel electrophorese as described in Example 3. Staining of the protein bands reveals that the bifunctional protein is located in the sediment from the disruption. The sediment is washed several times with chaotropic buffers and finally with water, resulting in further enrichment of the desired protein. The protein concentration is then determined in the aqueous protein suspension. The suspension is now adjusted to a concentration of 5 M in guanidinium hydrochloride and 2 mM in dithiothreitol (DTT). The mixture is stirred under nitrogen for about 30 minutes and then diluted with 50 mM tris buffer (pH 8.5) so that the protein concentration is 100 μg/ml. It is now dialyzed against this tris buffer and, after two changes of the buffer, dialyzed against water. The protein treated in this way is sterile filtered and its biological activity is checked. It shows full biological action both in the interleukin-2-dependent CTLL 2 cell proliferation assay and in the human bone marrow assay. Mixed colonies of granulocytes and macrophages are observed in these.

The bifunctional protein can be further purified by interleukin-2-specific affinity chromatography. The protein is still active in both assays. In contrast, an *E. coli* extract of the untransformed strain W3110 which has been treated as described shows no activity.

Other conditions are expedient for the industrial preparation of the product, for example for the folding of the protein and its purification. Suitable purification processes—which are known per se—are ion exchange, adsorption, gel filtration and preparative HPLC chromatography.

I claim:

1. A bifunctional protein consisting of a biologically active interleukin-2 (IL-2) constituent and a biologically active granuloctye macrophage colony stimulating factor (GM-CSF) consituent, wherein
   said IL-2 constituent includes the complete amino acid sequence that encodes a natural IL-2 protein, and
   wherein said GM-CSF constituent includes the complete amino acid sequence that encodes a natural GM-CSF protein.

2. A bifunctional protein having a biologically active IL-2 constituent and a biologically active GM-CSF constituent, wherein the two biologically active protein constituents are linked by a bridge consisting of 1 to about 20 genetically encodable amino acids.

3. A protein as claimed in claim 2, wherein the bridge corresponds to the formula (II)

$$-Asp-(a)_x-Pro-  \quad (II)$$

wherein x is an integer from 1 to 18, and aa is a genetically encodable amino acid with the exception of cysteine.

4. A protein as claimed in claim 3, wherein $(aa)_x$ is the amino acid sequence selected from the group consisting of -Pro-Met-Ile-Thr-Thr-Tyr-Ala-Asp-Aspand -Pro-Met-Ile-Thre-Thre-Tyr-Leu-Glu-Glu-Leu-Thr-Ile-Asp-Asp-.

5. A protein as claimed in claim 2, wherein the IL-2 constituent is arranged at the N-terminal end of the protein and the GM-CSF constituent is arranged at the C-terminal end of the protein.

6. A protein as claimed in claim 3, wherein the IL-2 constituent is arranged at the N-terminal end of the protein and the GM-CSF constituent is arranged at the C-terminal end of the protein.

7. A protein as claimed in claim 4, wherein the IL-2 consistuent is arranged at the N-terminal end of the protein and the GM-CSF constituent is arranged at the C-terminal end of the protein.

8. A composition comprising a bifunctional protein according to claim 1, and a pharmaceutically acceptable carrier.

9. A composition comprising a bifunctional protein according to claim 2, and a pharmaceutically acceptable carrier.

10. A composition comprising a pharmaceutically effective amount of a protein as claimed in claim 3, and a pharmaceutically acceptable carrier.

11. A composition comprising a pharmaceutically effective amount of a protein as claimed in claim 4, and a pharmaceutically acceptable carrier.

12. A composition comprising a pharmaceutically effective amount of a protein as claimed in claim 5, and a pharmaceutically acceptable carrier.

13. A composition comprising a pharmaceutically effective amount of a protein as claimed in claim 6, and a pharmaceutically acceptable carrier.

14. A composition comprising a pharmaceutically effective amount of a protein as claimed in claim 7, and a pharmaceutically acceptable carrier.

UNITED STATES PATENT AND TRADEMARK OFFICE
CERTIFICATE OF CORRECTION

PATENT NO. : 5,359,035
DATED : October 25, 1994
INVENTOR(S) : Paul HABERMANN

It is certified that error appears in the above-indentified patent and that said Letters Patent is hereby corrected as shown below:

Claim 3, column 6, line 17, "-Asp-(a)$_x$-Pro-" to ---Asp-(aa)$_x$-Pro---.

Claim 4, colunm 6, line 30, "-Thre-Thre-" to ---Thr-Thr---.

Signed and Sealed this

Twenty-fifth Day of April, 1995

Attest:

BRUCE LEHMAN

Attesting Officer

Commissioner of Patents and Trademarks